United States Patent [19]

Chalmin et al.

[11] Patent Number: 5,673,822
[45] Date of Patent: Oct. 7, 1997

[54] DEVICE FOR DROPWISE DELIVERY OF A FLUID CONTAINED IN A FLEXIBLE VIAL

[75] Inventors: Patrice Chalmin, Chatel Guyon; Jean Gazzola, Clermont Ferrand, both of France; Arthur Lifshey, East Brunswick, N.J.

[73] Assignee: Laboratoires Merck Sharp & Dohme-Chibret, Paris, France

[21] Appl. No.: 464,665

[22] PCT Filed: Jan. 5, 1994

[86] PCT No.: PCT/EP94/00020

§ 371 Date: Jun. 21, 1995

§ 102(e) Date: Jun. 21, 1995

[87] PCT Pub. No.: WO94/15855

PCT Pub. Date: Jul. 21, 1994

[30] Foreign Application Priority Data

Jan. 8, 1993 [FR] France .................. 93 00207
Sep. 21, 1993 [FR] France .................. 93 11430

[51] Int. Cl.$^6$ ........................................ B67D 5/06
[52] U.S. Cl. ................................ 222/183; 222/214
[58] Field of Search ........................ 222/160, 183, 222/212, 214, 325, 420

[56] References Cited

U.S. PATENT DOCUMENTS 2,873,884 2/1959 Goldfarb et al. ............... 222/214
3,506,004 4/1970 Mann et al. .
3,583,607 6/1971 Beck .
3,664,554 5/1972 Shiozawa ........................ 222/183
3,698,604 10/1972 Nigro .
4,067,499 1/1978 Cohen .............................. 222/105
4,634,023 1/1987 Tanaka et al. .
5,016,781 5/1991 Ten Wolde ...................... 222/183

FOREIGN PATENT DOCUMENTS 2312421 12/1976 France .
2647090 11/1990 France .

Primary Examiner—Philippe Derakshani
Attorney, Agent, or Firm—Sylvia A. Ayler; John J. Thompson; Mark R. Daniel

[57] ABSTRACT

The present invention provides a device for the dropwise delivery of a fluid (6) contained in a flexible vial (4; 4'), the device comprising a tubular case (1) capable of surrounding the vial (4; 4'), which casing is provided with a bottom portion (2; 7) whose inner surface lies opposite the outer surface of the bottom wall (42; 42') of the vial (4; 4'), the bottom portion (2; 7) of the casing (1) being equipped with a resiliently displaceable tab (3; 8) which can be moved so as to press against the bottom wall (42; 42') of the vial (4; 4') in order to squeeze the vial (4; 4') and drive out a drop (60) of fluid.

13 Claims, 2 Drawing Sheets

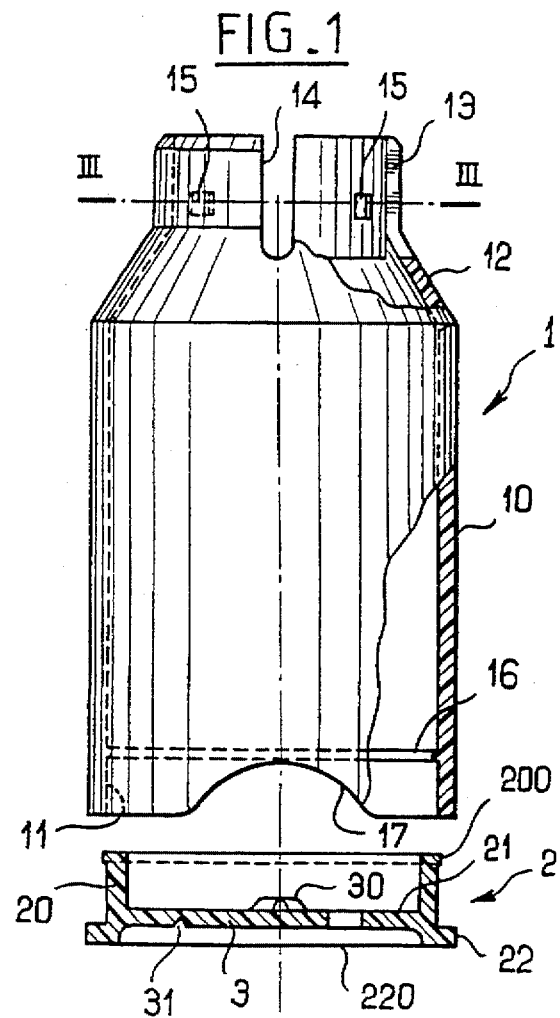
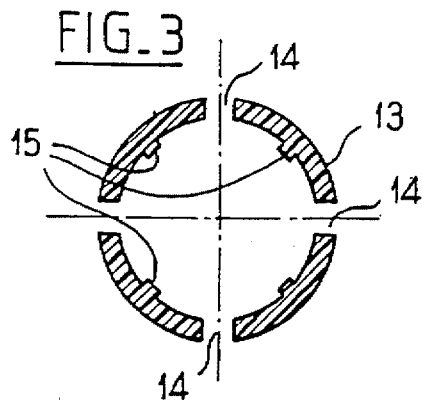
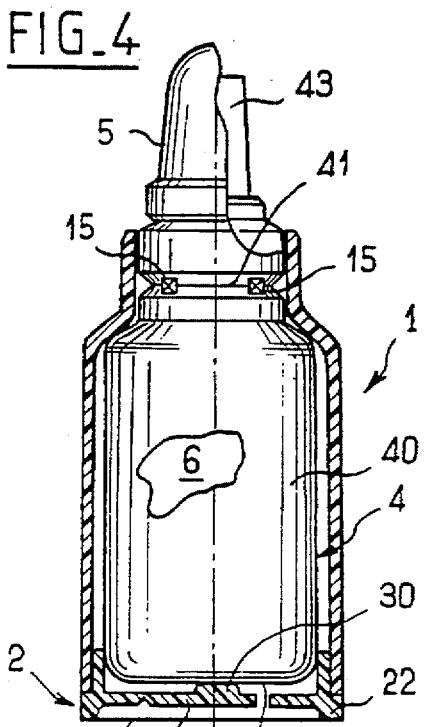
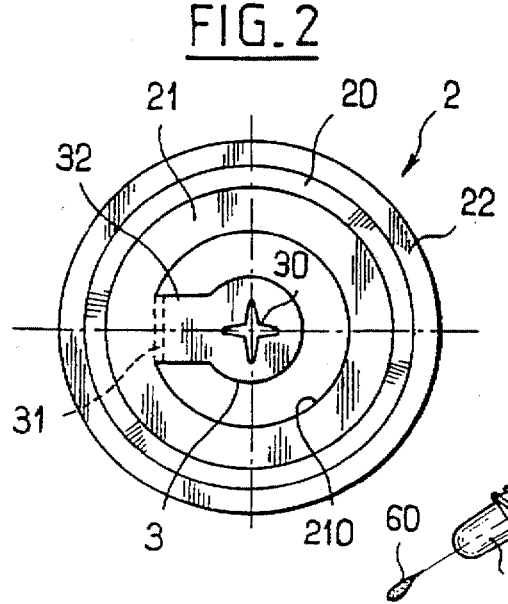
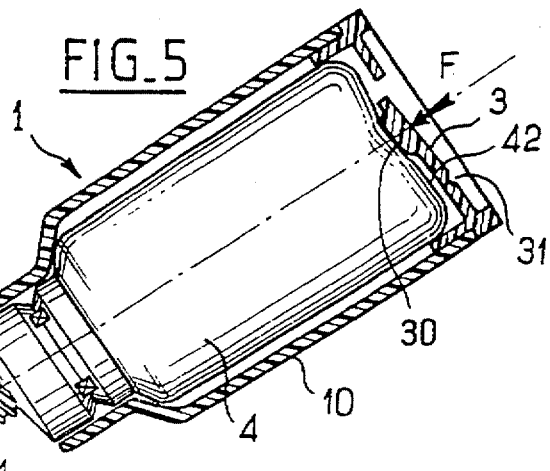

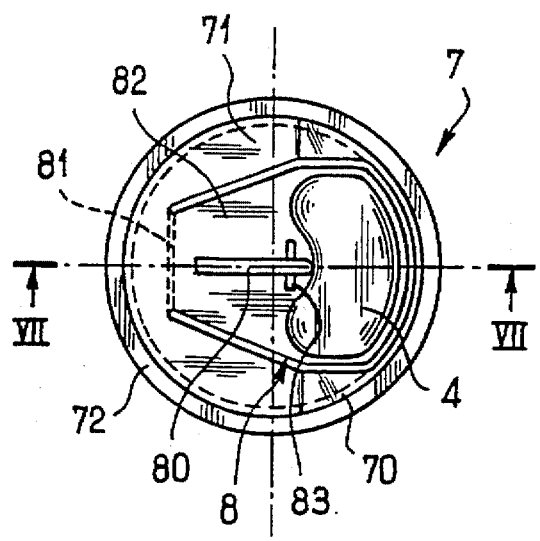
FIG_6
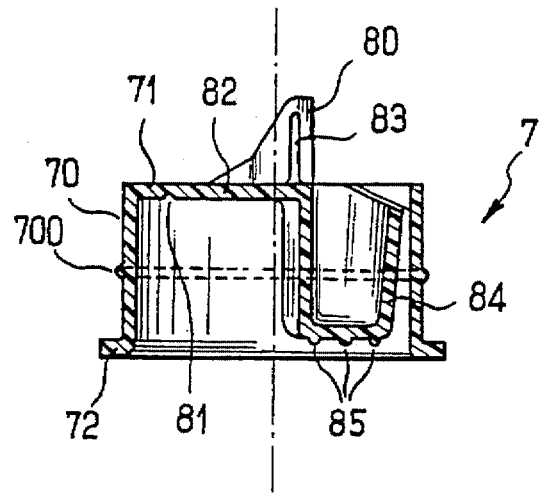
FIG_7
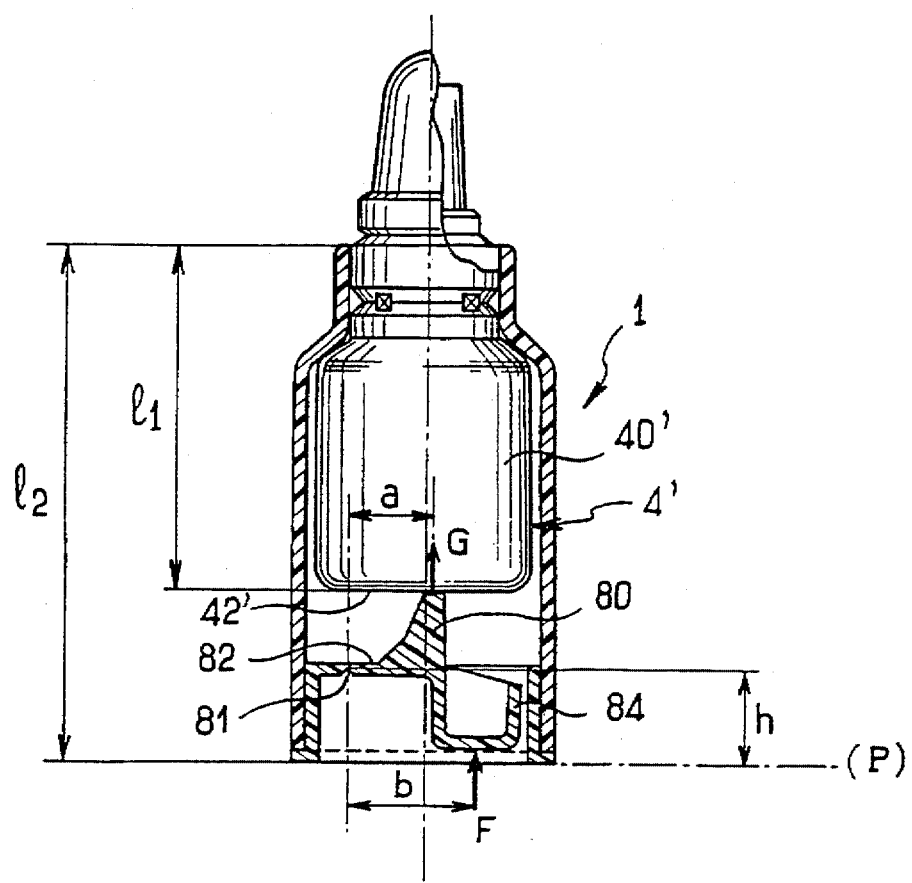
FIG_8

DEVICE FOR DROPWISE DELIVERY OF A FLUID CONTAINED IN A FLEXIBLE VIAL

BACKGROUND OF THE INVENTION

This invention relates to a device for delivering drop by drop a fluid, for example a medicinal or cosmetic liquid, contained in a flexible vial.

The fluid may be, for example, an eye lotion designed to be instilled into the eye of a user by the user himself.

Generally, vials which contain this type of product are flexible and thin walled vials made of synthetic material, whose dispensing neck (or nozzle) is equipped with a screwed stopper and a protective cap.

When using the vial as an eye dropper, the user firstly removes the cap and the stopper. Then, holding the vial in one hand, the user positions it above the eye to be treated, in an inverted or semi-inverted position, in order to direct the nozzle towards the ocular sac. To expel the eye lotion, the user manually squeezes the wall of the body or bottom of the vial. The resulting pressure within the vial drives out a certain quantity of product which exits the vial via the nozzle and normally descends into the eye at which it was aimed.

Although seemingly straightforward, such an operation can not always be performed satisfactorily.

In fact, the user cannot readily control the precise instant when the product is to be expelled from the vial, nor the number of drops to be delivered. In this respect, it is notable that the simple inversion of the vial, combined with the slight warming effect to which the product is subjected from contact of the user's hands with the vial and with a certain unintentional and uncontrolled squeezing with the fingers, is sufficient to cause one or several drops to descend unexpectedly and unintentionally into the eye or onto the region adjacent thereto. This problem is even more pronounced when a small vial is being used as handling thereof is correspondingly more difficult.

Subsequently, during the delivery operation itself, the quantity of product delivered depends on the intensity and duration of squeezing, which means that the quantity delivered may vary from one person to another and also, for the same user, from one instillation to another. A drawback with this is that a certain amount of the product, which is often expensive, is unavoidably wasted.

A more important drawback is connected with the fact that the dose prescribed to the patient must often be accurately adhered to. If the quantity which is effectively delivered is insufficient, the treatment may not be efficient. On the other hand, if the quantity delivered is too large, the surplus may, in certain cases, cause side effects. For example, an excess volume of eye lotion, not absorbed by the surface of the eye, may pass, via the tear duct, into the mouth, then into the oesophagus and stomach of the patient. The ingestion of excessive amounts of certain eye lotions can, indeed, sometimes present a hazard, particularly when they contain, for example, such ingredients as beta-blocking agents.

Accordingly, it is important to be able to administer to the user the exact dose of the product required. In many cases, this means one drop, and one drop only, of the solution.

The main object of this invention is to achieve the desired result by means of an inexpensive and light device which is easy to use, even for elderly people, or people with impaired manipulative skills.

SUMMARY OF THE INVENTION

The present invention accordingly provides a device for the dropwise delivery of a fluid, suitably a medicinal or cosmetic liquid, contained in a flexible vial, the device comprising a tubular casing capable of surrounding the vial, which casing is provided with a bottom portion whose inner surface lies opposite the outer surface of the bottom wall of the vial, the bottom portion of the casing being equipped with a resiliently displaceable tab which can be moved so as to press against the bottom wall of the vial in order to squeeze the vial and drive out a drop of fluid.

Furthermore, according to a certain number of advantageous but non-limiting features of this invention:

the bottom portion of the casing is removable;

this bottom portion is fitted into the tubular casing;

the tubular casing has at its top end, i.e. at the opposite end from the bottom portion, an open neck member which is equipped with vial neck retaining means;

these means consist of ratchetable pins or lugs which can engage a channel provided in the vial neck;

the resiliently displaceable tab is an integral part of the bottom portion of the casing, which is made of plastic material;

the tab is linked to the rest of the bottom portion via a less resistant, i.e. more flexible, and preferably groove-like, area which forms a hinge;

the tab is provided with a protrusion which comes into contact with the bottom wall of the vial;

this protrusion consists of a relatively large or elongate point which runs axially and thereby allows vials of reduced height to be used;

this protrusion is held by a tab member which is positioned inside the casing at a certain distance from the plane of the end face of the bottom portion;

this tab member is equipped with a button providing a surface which can be pushed using a finger and which is located at or adjacent to the plane of the end face of the bottom portion;

this button is an extension of the wall of the tab member;

the relative positions of the protrusion and the button with respect to the hinge area are such that they co-operatively provide a reduction in the amount of effort required to push against the vial using a finger; and the vial body and tubular casing body have a cylindrical shape.

DESCRIPTION OF THE DRAWINGS

Other features and advantages of this invention will become apparent from the embodiments described below by way of example and with reference to the accompanying drawings, in which:

FIG. 1 is a partial cross-sectional front elevation of the casing and its bottom portion, the latter not being fitted into the casing;

FIG. 2 is a top view of the bottom portion of the casing;

FIG. 3 is a cross-sectional view of the Vial neck taken along line III—III in FIG. 1;

FIG. 4 is a partially exploded view of a vial mounted in the casing of FIG. 1, represented as a cross-section;

FIG. 5 is a similar view to that of FIG. 4, displaying the whole unit during the process of instillation of a drop of liquid;

FIG. 6 is a top view of an alternative bottom portion to that depicted in FIG. 2;

FIG. 7 is a front view of the bottom portion taken as a vertical cross-section along the line VII—VII in FIG. 6; and FIG. 8 is a similar view to that of FIG. 4, where the device is represented with the bottom portion shown in FIGS. 6 and 7 and including a vial of reduced height.

Casing 1 as represented in the drawings is a tubular casing suitably made of semi-rigid plastic material, comprising a cylindrical body 10, a generally cylindrical neck 13 having a smaller diameter, and a truncated cone-shaped coupling part 12 which links parts 10 and 13. The smooth inner wall of the casing body is referenced 11. It is provided with an internal thin rib 16 located near the bottom end of the body 10, i.e. at the opposite end of the body 10 from the neck 13. This end has a pair of diametrically opposite indentations or recesses 17 with a curved contour, the function of which is explained below.

Neck 13 incorporates four longitudinal recesses in the shape of ports which open out at the end of the neck. These recesses are disposed at 90° intervals. They thus delimit flexible tabs, which provides a certain resiliency to the body 13 in the radial direction. Each one of these tabs has, on its inner wall, a small protrusion or pin 15. The four pins or lugs are located at the same level.

DETAIL DESCRIPTION OF THE INVENTION

Casing 1 is linked to the bottom portion 2. The latter is suitably made out of plastic material, typically of the same material as that used for the casing. The bottom portion 2 comprises a circular shaped bottom wall 21, a cylindrical part 20 whose height is small, and an end flange 22. The free end of the wall 20, opposite the flange 22, has a thin circumferential rib 200 on its outer surface. The bottom portion 2 is so shaped that it can be fitted into the end part of the casing body 10. In order to achieve satisfactory coupling, rib 200 slides past rib 16, so that the bottom portion 2 is forced into the casing 1. However, it is possible to remove the bottom portion 2 if necessary by submitting the latter to axial pull. The function of the recesses 17 is thus to allow the fingers to be placed on the bottom portion 2 in order to perform this pull.

According to an essential feature of this invention, a resiliently displaceable tab 3 is provided in the bottom portion 2. This tab is an integral part of the wall 21, being suitably moulded with the latter. It generally has a circular shape and is positioned in an opening 210, also circular, made in the bottom wall 21. Tab 3 comprises a part 32 which allows it to be linked to the wall 21 via a grooved area 31 which is less resistant. This area gives the tab its flexibility, playing the role of a small hinge.

The tab 3 has a protrusion 30 in its centre, which is located at a point corresponding to the longitudinal axis of the bottom portion 2 and the casing 1. This protrusion, which is also ideally an integral part of the rest of the tab 3, is in, for example, the shape of a four-pointed star as depicted in FIG. 2. Protrusion 30 is situated on the face of the tab 3 directed towards the inside of the casing body 10.

This device has been designed to receive a flexible walled vial 4 containing a fluid 6 such as a medicinal or cosmetic liquid, e.g. eye lotion.

The vial 4 is generally provided with a dispensing nozzle 44 onto which a tapped stopper 43 is screwed. This stopper can itself be covered by a protective cap 5.

In certain applications, the tapped stopper 43 is equipped with locking members, in which case the protective cap 5 becomes unnecessary.

The device is conformed and dimensioned such that the vial can be intimately housed within the casing with minimal play, as can be seen from FIG. 4. Vial 4 is of course placed in the casing body 10 before the bottom portion 2 is fitted onto the casing.

The pins or lugs 15 are positioned and dimensioned such that when the vial 4 is correctly housed within the casing 1, they ratchet in the channel 41 provided on the vial neck 13. This ratcheting is made possible by the resiliency of the neck 13 of the casing in view of the presence of the ports 14.

In FIG. 4, the cylindrical wall of the vial body is referenced 40 and the bottom wall of the vial body is referenced 42. Ideally, both walls are thin and very flexible. Once the vial has been placed in the device, the protrusion 30 of the tab 3 is closely in contact with the central area of the bottom wall 42 of the vial.

In this respect, it should be noted that the presence of the flange 22 serves as a stop to restrict any inward propulsion of the bottom portion 2 into the casing 1, thereby preventing the tab 3 from pressing against the bottom wall 42 of the vial when the device is not in use. It should also be noted that this flange has a flat inner face 220 as a result of which the device can be placed vertically on a supporting surface, e.g. on a table.

Referring to FIG. 5, the use of the device by a patient for the instillation of a predetermined quantity of drops of eye lotion 6 into the eye is accomplished by the following method.

After having removed the cap 5 and stopper 43, the user first uncovers the dispensing nozzle 44. The user then tilts the device into the desired position, for example the semi-inverted position as shown in FIG. 5, and brings the nozzle 44 directly above the eye into a position which is appropriate for instillation.

It should be noted that this handling operation is performed without any contact between the fingers and the flexible walls of the vial 4. Thus, the potentially uncontrolled squeezing of the device with the fingers is exclusively absorbed by the wall of the casing 1 which is relatively rigid. Furthermore, the product contained in the vial is not warmed up. No unwanted drops of liquid can thus unexpectedly escape the vial.

The user then presses the tab 3 with one finger, as is symbolized by arrow F in FIG. 5. The tab 3 slightly bends around the hinge area 31 and squeezes the bottom wall 42 of the vial via the protrusion 30. This causes over-pressure within the vial, thereby permitting a certain quantity of the product to be expelled.

As will be appreciated, the distance through which the tab 3 may be pushed in is limited, not least because the finger used for pushing will eventually come into contact with the circular edge of the annular bottom wall 21; the stroke of the tab 3 is of course ideally determined such that only one drop 60 is expelled. If the user wants to expel several drops, this can only be achieved by successively pressing the tab 3, each press delivering one individual drop.

The delivered dose is thus extremely well controlled.

This invention also allows the manufacturer to realise a certain number of advantages. In particular, it is possible to reduce the thickness of the vial wall and to use nozzles with a larger orifice diameter, thus making the moulding technique easier. Indeed, until now the tendency was to reduce the diameter of the delivery orifice as much as possible so as to avoid the problem of unexpected loss of product drops when handling conventional vials.

The bottom portion 7 as shown in the version represented in FIGS. 6 and 7 has been more specifically designed for a device intended to take vials with a small volume (and correspondingly with reduced height).

The bottom portion 7 is in the shape of a stopper and composed of a cylindrical body 70 equipped with a bottom wall 71 and a flange 72. It suitably consists of a single injection moulded plastic piece, which is able to fit into the open end of the casing 1. A peripheral rib 700 ensures a tight fit to the coupling. The flange 72 serves as a stop limiting the member 7 from pushing into the casing 1.

A considerable part of the bottom wall 71 is occupied by a flexible tab 8. The latter comprises a flat member 82 which is linked to the rest of the bottom wall 71 by a small grooved area 81 forming a hinge.

On the inside of the casing the member 82 has a protrusion 80. It consists of a relatively long pointed strip reinforced by lateral ribs 83. The open end of the protrusion is located near the central axis of the bottom portion 7. Beyond the protrusion the tab takes the form of a hollow bowl or extension 84, the bottom part of which is in the opposite direction to the protrusion, i.e. towards the outside of the casing.

For information purposes, the diameter of the body 70 is of the order of 25 millimetres and the length of the protrusion 80 is of the order of 6 millimetres.

As can be seen in FIG. 8, the flat portion 82 of the tab 8 is positioned inside the casing 1 at a certain distance h, for example of the order of 10 millimetres, from the end plane P of the bottom portion.

On the other hand, the bottom of the bowl 84 is located at or near to this plane, so that it is easily accessible by the user's finger. The contours 85 in the form of ridges have been specially designed on the bottom of the bowl to improve finger contact and avoid slipping.

The extension 84 acts as a button. By using a finger to apply an axial force E, this is then transmitted by means of the hinge 81 to the protrusion 80. This in turn exerts a force G against the bottom wall 42' of the vial 4', in the central area of the bottom wall (see FIG. 8).

Owing to the fact that the force F is applied at a distance b from the hinge 81, which is greater than the distance a separating the force G from this hinge, the transmission of forces takes place with a reduction ratio b/a. This can be expressed as G=F×b/a.

By simply looking at FIG. 8 it can be seen that the device adjusts in order to use vials 4' whose bodies 40' have a small volume and a correspondingly smaller height $l_1$. The device, however, has a somewhat larger height $l_2$ and thus can readily accommodate vials of height $l_2$ by the simple expedient of exchanging bottom portion 7 for bottom portion 2. In addition, in view of the reduction in force which needs to be applied, as discussed above, the user consequently does not need to exert an excessive amount of effort in order to release individual drops from the vial.

Claims:

1. A device for the dropwise delivery of a fluid (6) contained in a flexible vial (4; 4'), the device comprising a tubular casing (1) capable of surrounding the vial (4; 4'), which casing is provided with a bottom portion (2; 7) whose inner surface lies opposite the outer surface of the bottom wall (42; 42') of the vial (4; 4') the bottom portion (2; 7) of the casing (1) being equipped with a resiliently displaceable tab (3; 8) which is linked to the rest of (21; 71) the bottom portion (2; 7) via an area (31; 81) which is less resistant to a force and serves as a hinge, the resiliently displaceable tab (3; 8) which can be moved so as to press against a bottom wall (42; 42') of the vial (4; 4') in order to squeeze the vial (4; 4') and drive out a drop (60) of fluid.

2. A device as claimed in claim 1 wherein the bottom portion (2; 7) of the casing (1) is removable.

3. A device as claimed in claim 2 wherein the bottom portion (2; 7) is fitted into the tubular casing (1).

4. A device as claimed in any one of the preceding claims wherein the tubular casing (1) has at its top end, i.e. at the opposite end from the bottom portion (2; 7), an open neck member (13) equipped with means (15) for retaining the neck of the vial (4; 4').

5. A device as claimed in claim 4 wherein the vial neck retaining means (15) are pins which can engage a channel (41) provided in the neck of the vial (4; 4').

6. A device according to claim 1 wherein the resiliently displaceable tab (3; 8) is an integral part of the bottom portion (2; 7) of the casing (1), the latter being made of plastic material.

7. A device according to claim 1 wherein the tab (3; 8) is provided with a protrusion (30; 80) which comes into contact with the bottom wall (42; 42') of the vial (4; 4').

8. A device as claimed in claim 7 wherein the protrusion (80) consists of a relatively large point running axially.

9. A device as claimed in claim 8 wherein the protrusion (80) is held by a tab member (82) which is positioned inside the casing (1) at a certain distance (h) from the plane (P) of the end face of the bottom portion (2; 7).

10. A device as claimed in claim 9 wherein the tab member (82) is equipped with a button (84) providing a surface which can be pushed using a finger and which is located at or adjacent to the plane (P) of the end face of the bottom portion (2; 7).

11. A device as claimed in claim 10 wherein the button (84) forms an extension of the wall of the tab member (82).

12. A device as claimed in claim 10 or claim 11 wherein the relative positions of the protrusion (80) and of the button (84) with respect to the hinge area (81), are such that they co-operatively provide a reduction in the amount of effort required to push against the vial using a finger.

13. A device according to claim 1 wherein the body (40; 40') of the vial (4; 4') and the body (10) of the tubular casing (1) have a cylindrical shape.

* * * * *